(12) United States Patent
Macduff

(10) Patent No.: US 9,370,430 B2
(45) Date of Patent: Jun. 21, 2016

(54) BIO-MECHANICAL PROSTHETIC FULL FINGER

(71) Applicant: RCM Enterprise, L.L.C., Tumwater, WA (US)

(72) Inventor: Charles Colin Macduff, Olympia, WA (US)

(73) Assignee: RCM Enterprise, LLC, Tumwater, WA (US)

( * ) Notice: Subject to any disclaimer, the term of this patent is extended or adjusted under 35 U.S.C. 154(b) by 0 days.

(21) Appl. No.: 14/230,095

(22) Filed: Mar. 31, 2014

(65) Prior Publication Data

US 2014/0303749 A1    Oct. 9, 2014

Related U.S. Application Data

(60) Provisional application No. 61/806,772, filed on Mar. 29, 2013.

(51) Int. Cl.
*A61F 2/54* (2006.01)
*A61F 2/80* (2006.01)
(Continued)

(52) U.S. Cl.
CPC .............. *A61F 2/4241* (2013.01); *A61F 2/586* (2013.01); *A61F 2002/587* (2013.01); *A61F 2002/7862* (2013.01)

(58) Field of Classification Search
CPC .... A61F 2/586; A61F 2002/587; A61F 5/013
USPC ........................................ 623/63–64; 602/22
See application file for complete search history.

(56) References Cited

U.S. PATENT DOCUMENTS

| 319,776 A | 6/1885 | Bashore |
| 984,179 A | 2/1911 | Aydt |

(Continued)

FOREIGN PATENT DOCUMENTS

| GB | 110333 A | 10/1917 | | |
| GB | 2488365 A | * 8/2012 | ................ | A61F 2/58 |
| JP | 2002-345861 A | * 12/2002 | ................ | A61F 2/56 |

OTHER PUBLICATIONS

Leow, M., et al. "Optimal Circumference Reduction of Finger Models for Good Prosthetic Fit of a Thimble-Type Prosthesis for Distal Finger Amputations", Journal of Rehabilitation Research and Development, Mar. 2001, vol. 38, No. 2; pp. 273-279.

(Continued)

*Primary Examiner* — David H Willse
(74) *Attorney, Agent, or Firm* — James A. Sheridan; Sheridan Law, LLC

(57) ABSTRACT

There is disclosed a prosthetic full finger assembly. In an embodiment, the assembly includes a distal phalanges. The assembly further includes a middle phalanges having an operable connection with the distal phalanges. The assembly includes a proximal phalanges ring having an operable connection with the middle phalanges. The assembly includes a proximal phalanges yoke having an operable connection with the proximal phalanges ring. The assembly includes a metacarpal back plate having an operable connection with the proximal phalanges yoke and an operable connection with the proximal phalanges ring. The assembly includes an anchoring portion having an operable connection with the metacarpal back plate at a location proximal of the operable connection of the proximal phalanges ring. Other embodiments are also disclosed.

16 Claims, 11 Drawing Sheets

(51) Int. Cl.
*A61F 2/42* (2006.01)
*A61F 2/58* (2006.01)
*A61F 2/78* (2006.01)

(56) References Cited

U.S. PATENT DOCUMENTS

| | | | |
|---|---|---|---|
| 2,706,296 | A | 4/1955 | Fletcher et al. |
| 2,867,819 | A | 1/1959 | George |
| 3,483,718 | A | 12/1969 | Lodrini |
| 3,707,963 | A * | 1/1973 | Keropian ............ 602/21 |
| 4,997,433 | A | 3/1991 | Goble et al. |
| 5,062,855 | A | 11/1991 | Rincoe |
| 5,941,914 | A | 8/1999 | Jacobsen et al. |
| 6,908,489 | B2 | 6/2005 | Didrick |
| 8,337,568 | B2 | 12/2012 | Macduff |
| 2004/0054424 | A1 | 3/2004 | Matsuda |
| 2005/0043822 | A1 | 2/2005 | Didrick |
| 2006/0224249 | A1 | 10/2006 | Winfrey |
| 2010/0082103 | A1 | 4/2010 | Blunn et al. |
| 2011/0144770 | A1 | 6/2011 | Moyer et al. |
| 2012/0330432 | A1 | 12/2012 | Fong |
| 2013/0268094 | A1 | 10/2013 | Van Wiemeersch |
| 2014/0371897 | A1 | 12/2014 | Lin et al. |

OTHER PUBLICATIONS

Cabibihan, J. "Patient-Specific Prosthetic Fingers by Remote Collaboration—a Case Study", PLoS ONE, May 2011, vol. 6, No. 5.
International Search Report and Written Opinion for PCT/US16/16215, Apr. 22, 2016, 8 pp.

* cited by examiner

BIO-MECHANICAL PROSTHETIC FULL FINGER

This application claims the benefit under 35 U.S.C. 119(e) of U.S. Provisional Patent Application No. 61/806,772, filed Mar. 29, 2013 by Charles Colin Macduff for "Bio-Mechanical Prosthetic Full Finger (BPFF), formally known as the Mechanical Finger Ring (MFR)," which patent application is hereby incorporated herein by reference.

BACKGROUND

If a person loses a finger, a finger segment, or a fingertip, the result is impaired performance of the hand. Having an amputated finger inhibits an amputee from performing some of the most basic tasks. For example, with a lost finger or fingertip, the task of typing on a computer or simply dialing on a phone becomes significantly difficult. These types of tasks require the actions with precision that only fingers are able to offer. Not only do fingers allow people to perform precise actions, but fingers also provide people with an increased ability to handle items. While holding an item in one hand, the weight of the item is dispersed through all of a user's fingers. By simply varying the force used by each finger on the holder's hands, the holder is able to manipulate the item in a myriad of ways. However, if the holder is missing a single finger, the amount of precision for the manipulation and the number of ways the holder can manipulate the item is decreased. The present invention is a device that acts as a prosthetic substitute of the lost portion of a finger. The present invention is designed to bend and naturally mimic a real finger. Additionally, the present invention comprises a metal thread looped about the tip of the finger to allow the users to interact with a capacitive type of touch screen.

SUMMARY

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

In an embodiment, there is provided a prosthetic full finger assembly, including a distal phalanges; a middle phalanges having an operable connection with the distal phalanges; a proximal phalanges ring having an operable connection with the middle phalanges; a proximal phalanges yoke having an operable connection with the proximal phalanges ring; a metacarpal back plate having an operable connection with the proximal phalanges yoke and an operable connection with the proximal phalanges ring; and an anchoring portion having an operable connection with the metacarpal back plate at a location proximal of the operable connection of the proximal phalanges ring.

In another embodiment, there is provided a prosthetic full finger assembly, including a distal phalanges having an operable connection at a proximal end thereof; a metacarpal back plate having an operable connection adjacent a distal end thereof and an anchor adjacent a proximal end thereof; and articulation components configured between the metacarpal back plate and the distal phalanges; wherein the metacarpal back plate is configurable for placement on a back portion of a hand, when a metacarpal joint in the hand is bent the articulation components are articulated to articulate the distal phalanges.

Other embodiments are also disclosed.

The present invention relates generally to a prosthetic device, more specifically, to a prosthetic device designed for a full finger or full fingertip amputees.

Additional objects, advantages and novel features of the technology will be set forth in part in the description which follows, and in part will become more apparent to those skilled in the art upon examination of the following, or may be learned from practice of the technology.

BRIEF DESCRIPTION OF THE DRAWINGS

Non-limiting and non-exhaustive embodiments of the present invention, including the preferred embodiment, are described with reference to the following figures, wherein like reference numerals refer to like parts throughout the various views unless otherwise specified. Illustrative embodiments of the invention are illustrated in the drawings, in which.

DETAILED DESCRIPTION

Figure 1:
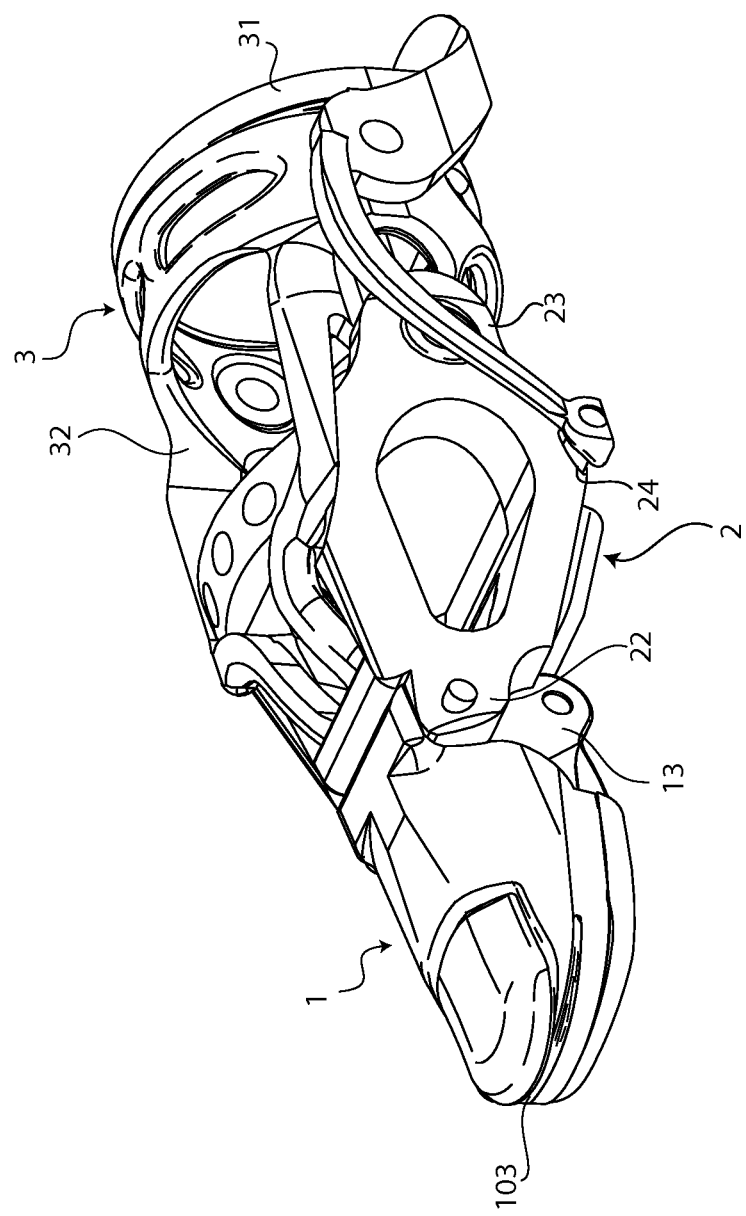
FIG. 1 is a perspective view of a prosthetic partial finger device.

Embodiments are described more fully below in sufficient detail to enable those skilled in the art to practice the system and method. However, embodiments may be implemented in many different forms and should not be construed as being limited to the embodiments set forth herein. The following detailed description is, therefore, not to be taken in a limiting sense.

The present invention is a prosthetic finger that can be fitted for a user with an amputated finger, fingertip, or finger segment. The prosthetic finger is a mechanical finger that is able to mimic the motions and functionalities of a real finger. The mechanical prosthetic finger comprises of three major components including a distal phalanges 1, a middle phalanges 2, and a proximal phalanges ring 3. A plurality of rods 8 and a series of hinges are used to secure the distal phalanges 1, the middle phalanges 2, and the proximal phalanges ring 3 together. The distal phalanges 1 is the tip segment of the prosthetic finger. The middle phalanges 2 is the middle segment of the prosthetic finger. The proximal phalanges ring 3 is the base of the prosthetic finger that anchors the entire prosthetic finger to the user's residual finger. As the level of amputation differs among each user, the present invention can be modified to be custom fit for each user. For example, users who have an amputated finger tip will be custom fitted with a prosthetic finger, where the middle phalanges 2 and the proximal phalanges ring 3 are frames that fit and mount to the user's residual finger. To provide the prosthetic finger with grip and a softer touch, the present invention additionally comprises a distal pad platform 4, a distal pad 5, a middle pad platform 6, and a middle pad 7. The distal pad 5 and the middle pad 7 are made from a soft texture that mimics the texture of a real finger. In the preferred embodiment of the present invention, to additionally contribute to the realistic aspect of the prosthetic finger, the present invention further comprises of a articulation cable 9 and a touch screen mechanism 10. The articulation cable 9 further provides the prosthetic finger with realistic curling motions. The touch screen mechanism 10 allows the user to use the prosthetic finger to operate touch screens. Although some touch screens, such as resistive touch screens, only require pressure for sensing the touch, other touch screens use the body's natural current to sense touch. These touch screens that require the user's natural body current are called capacitive touch screens. The touch screen mechanism 10 allows the user to conduct their own body current and direct it towards the tip of the prosthetic finger.

Figure 2:
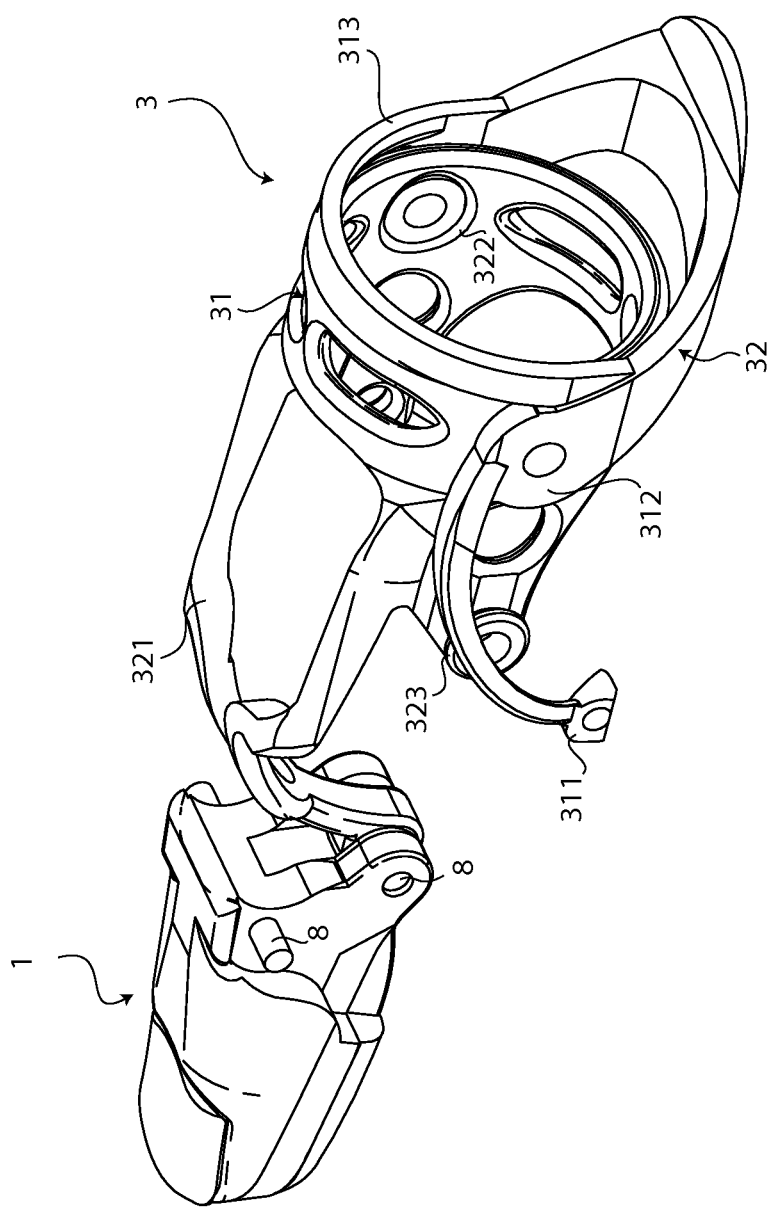
FIG. 2 is a view of the present invention without the middle phalanges showing the connection of the extended wishbone hinge to the pair of proximal pulling hinges.
Figure 3:
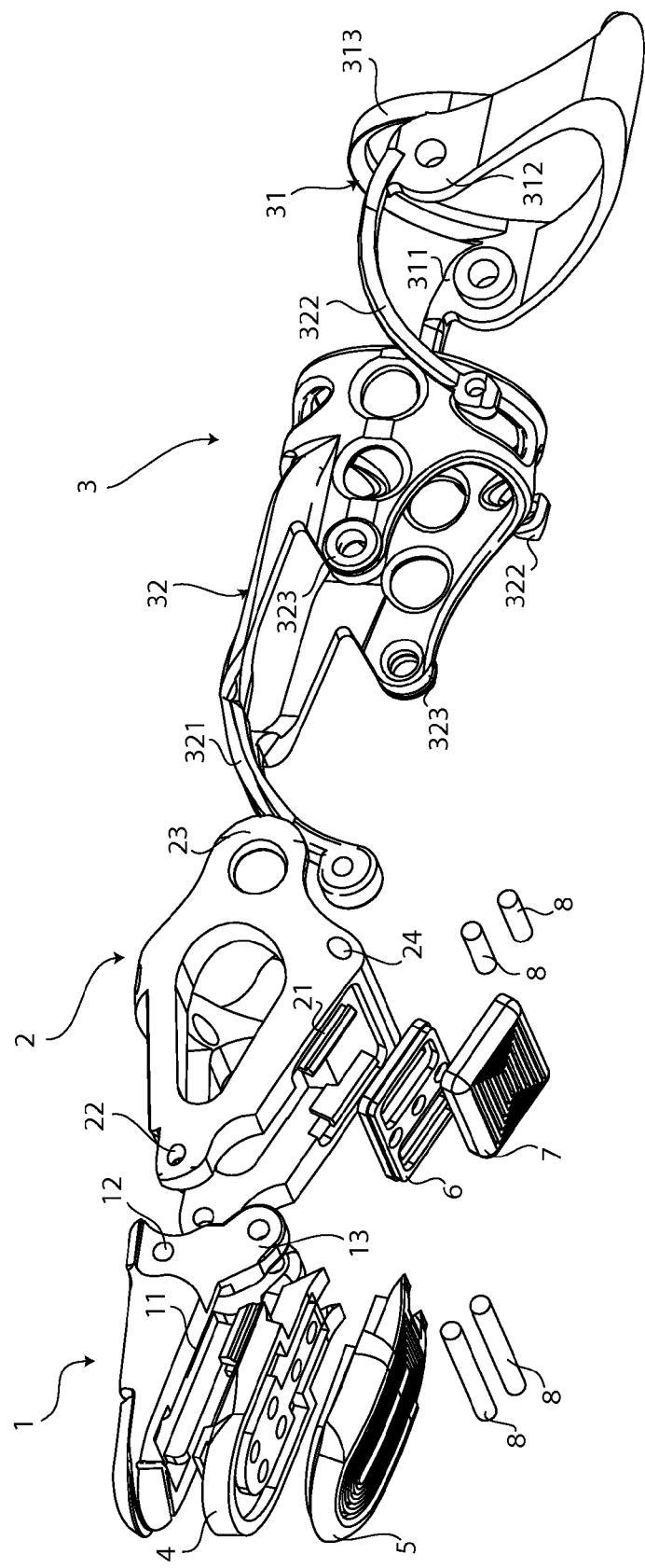
FIG. 3 is an exploded view of the present invention.

In reference to FIG. 1-3, the distal phalanges 1 comprises a distal platform fastener 11, a middle phalanges joint channel 12, and a pair of proximal pulling hinges. The distal pad 5 and the distal pad platform 4 are secured to the distal phalanges 1. The distal pad 5 is engaged and adhered to the distal pad platform 4 by a RTV silicone adhesive. The use of such an adhesive is important when using a silicone material for the distal pad 5 due to its high temperature material. The distal pad 5 is made from a soft material, such as silicone, to mimic the flesh of a real finger pad. The distal pad 5 is attached to the distal phalanges 1 by means of the distal pad platform 4. The distal pad platform 4 is secured to the distal platform fastener 11 of the distal phalanges 1. In the preferred embodiment of the present invention, the distal platform fastener 11 is a distal platform latch and the distal pad platform 4 comprises of a corresponding latch hole. However, in other embodiments of the present invention, the distal platform fastener 11 can simply be an adhesive. The distal platform fastener 11 is positioned on a lower distal surface of the distal phalanges 1. In comparison to a real finger, the positioning of the distal platform fastener 11 allows the distal pad 5 to be positioned where the finger pads of a real finger would be. The distal phalanges 1, the distal pad 5, and the distal pad platform 4 combine together to be shaped like a real finger tip. On the rear end of the distal phalanges 1 is the middle phalanges joint channel 12. The middle phalanges joint channel 12 is a hole that laterally traverses through the distal phalanges 1. The middle phalanges joint channel 12 provides a pivot point for the connection of the middle phalanges 2. The pair of proximal pulling hinges 13 is a pair of hinge channels that downwardly extends at an angle from the rear of the distal phalanges 1. The pair of proximal pulling hinges 13 are positioned adjacent to the middle phalanges joint channel 12. The pair of proximal pulling hinges 13 provides a pulling point for the proximal phalanges ring 3 to pull on to mimic the curling motion of a real finger.

In reference to FIG. 1-3, the middle phalanges 2 comprises a middle platform fastener 21, a pair of distal joint hinges 22, a pair of proximal joint hinges 23, and a pair of spring hinge ports 24. For a finger amputee with a missing finger tip, the middle phalanges 2 is a frame that wraps around the intermediate phalanges of the user's residual finger. The middle pad 7 and the middle pad platform 6 are secured to the middle phalanges 2. The middle pad 7 is engaged and adhered to the middle pad platform 6 by a RTV silicone adhesive. Similar to the distal pad 5, the middle pad 7 is made from a soft material, such as silicone. The middle pad 7 is attached to the middle phalanges 2 by means of the middle pad platform 6. The middle pad platform 6 is secured to the middle platform fastener 21 of the middle phalanges 2. In the preferred embodiment of the present invention, similar to the distal platform fastener 11, the middle platform fastener 21 is a middle platform latch and the middle pad platform 6 comprises of a corresponding latch hole. In other embodiments, the middle platform fastener 21 can be an adhesive. The middle platform fastener 21 is positioned on a lower middle surface of the middle phalanges 2. Similar to the distal phalanges 1, the positioning of the middle platform fastener allows the middle pad 7 to be positioned where the finger pads of the intermediate phalanges of a real finger would be. The middle phalanges 2, the middle pad 7, and the middle pad platform 6 combine together to be shaped like a real intermediate phalanges. The pair of distal joint hinges 22 is forwardly extended from the middle phalanges 2 in parallel relationship to each other. The pair of proximal joint hinges 23 is extended from the middle phalanges 2 in an opposite direction of the pair of distal joint hinges 22. As a result, the pair of distal joint hinges 22 and the pair of proximal joint hinges 23 are positioned on opposite ends of the middle phalanges 2. The middle phalanges 2 is able to jointly connect the distal phalanges 1 to the proximal phalanges ring 3 together by means of the pair of distal joint hinges 22 and the pair of proximal joint hinges 23.

In reference to FIG. 1-3, the proximal phalanges ring 3 is a two part component comprising of a proximal phalanges yoke 31 and a proximal phalanges frame 32. The proximal phalanges frame 32 is the body of the proximal phalanges ring 3 that anchors itself onto the user's finger. The proximal phalanges yoke 31 is the brace of the proximal phalanges ring 3 that provides support in the motion provided by the present invention. The proximal phalanges yoke 31 further comprises, a pair of extending spring hinges 311, a pair of frame joint hinges 312, and a finger base brace 313. The proximal phalanges frame 32 comprises an extended wishbone hinge 321, a pair of posterior yoke joint hinges, and a pair of anterior phalanges joint hinges 323. The finger base brace 313 is a circular frame that is the body of the proximal phalanges yoke 31. The finger base brace 313 is shaped to fit the base of the user's residual finger. The pair of frame joint hinges 312 is extended from the finger base brace 313. The pair of extending spring hinges 311 is a flat spring hinge that extends from the pair of frame joint hinges 312. The extended wishbone bone is shaped like a wishbone and is forwardly extending from the proximal phalanges frame 32. The pair of anterior phalanges joint hinges 323 is extended from the proximal phalanges frame 32 adjacent to the extended wishbone hinge 321. The pair of posterior yoke joint holes 322 are holes that laterally traverse through the proximal phalanges. The proximal phalanges yoke 31 is jointly connected to the proximal phalanges frame 32. The pair of frame joint hinges 312 is aligned and engaged to the pair of posterior yoke joint holes 322. The pair of frame joint hinges is able to jointly connect to the pair of posterior yoke joint holes 322 by means of a yoke stud. The yoke stud is inwardly protruding from each of the frame joint hinges. The proximal phalanges yoke 31 is then aligned and jointly secured to the pair of posterior yoke joint holes 322.

In reference to FIG. 1-3, the distal phalanges 1 is connected to the middle phalanges 2. The proximal phalanges ring 3 is connected to the middle phalanges 2 opposite of the distal phalanges 1. The plurality of rods 8 is traversed through the pair of distal joint hinges 22, the middle phalanges joint channel 12, the pair of proximal joint hinges 23, the pair of extending spring hinges 311, the extended wishbone hinge 321, and the pair of proximal pulling hinges for the assembly. The plurality of rods 8 consists of a first rod, a second rod, and a third rod. The pair of distal joint hinges 22 is aligned and secured to the middle phalanges joint channel 12 by the first rod. The pair of spring hinge ports 24 is aligned and secured to the pair of extending spring hinges 311 by the second rod. The extended wishbone hinge 321 is aligned and secured to the pair of proximal pulling hinges 13 by the third rod. The extended wishbone is extended over and traversed through the middle phalanges 2 for its connection to the pair of proximal pulling hinges 13. Each of the anterior phalanges joint hinges 323 comprises a middle stud. The middle stud is an outwardly protruding stud from each anterior phalanges joint hinge 323. The pair of anterior phalanges joint hinges 323 is aligned and jointly secured to the pair of proximal joint hinges 23 by the middle stud. All of the joint connections described provides the prosthetic finger the ability to curl and move like a real finger.

Figure 4:
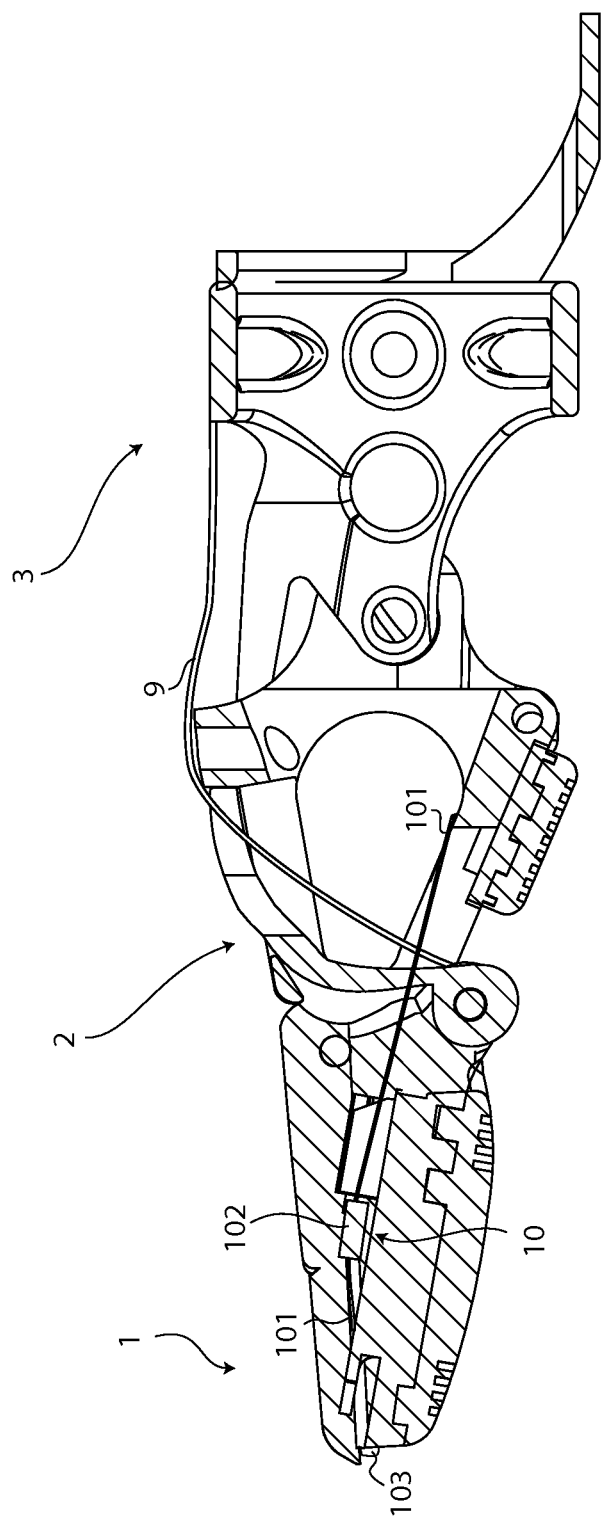
FIG. 4 is a cross sectional view of the present invention showing the articulation cable and the touch screen mechanism.
Figure 5:
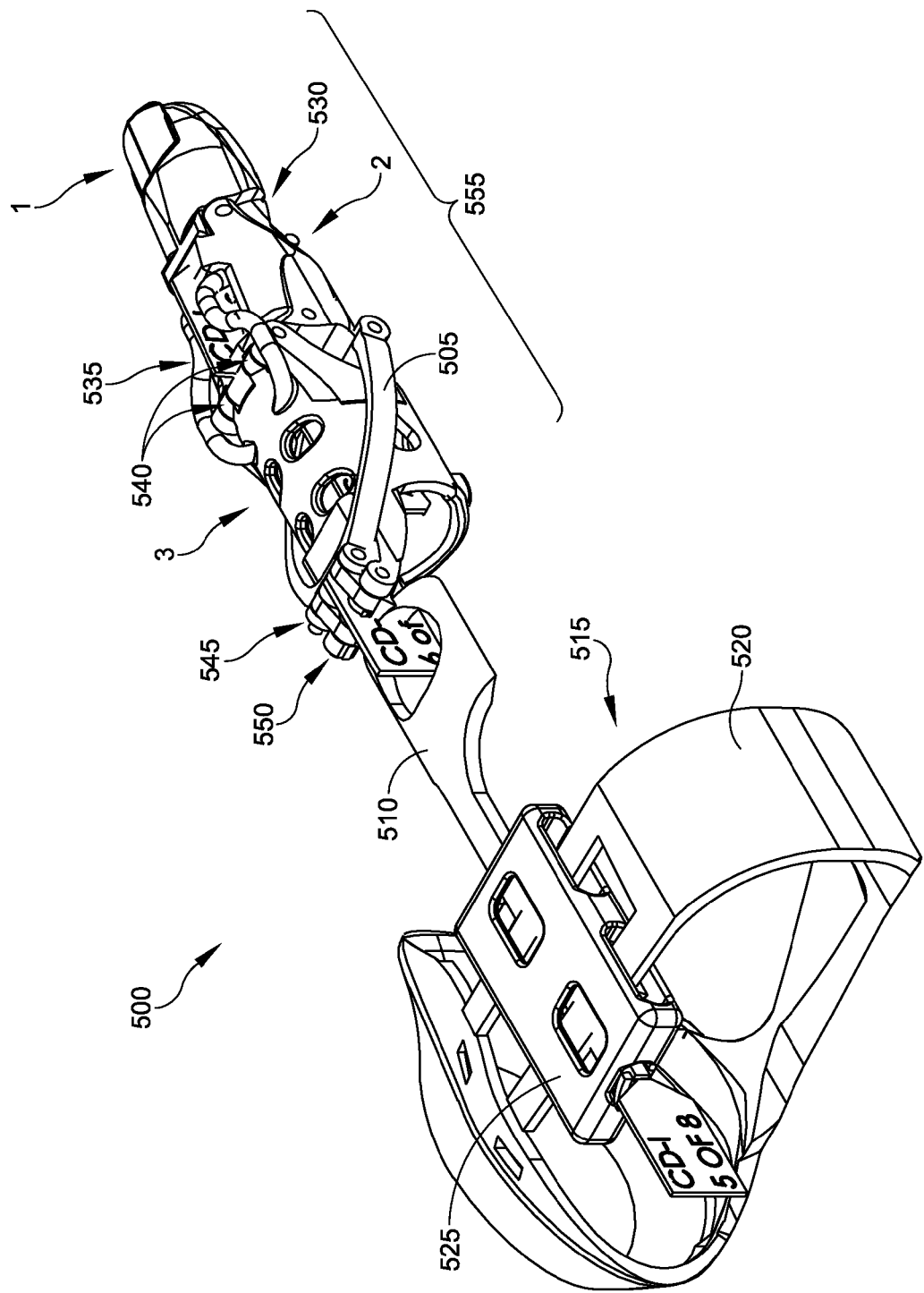
FIG. 5 is a perspective view of an embodiment of a prosthetic full finger assembly.
Figure 6:
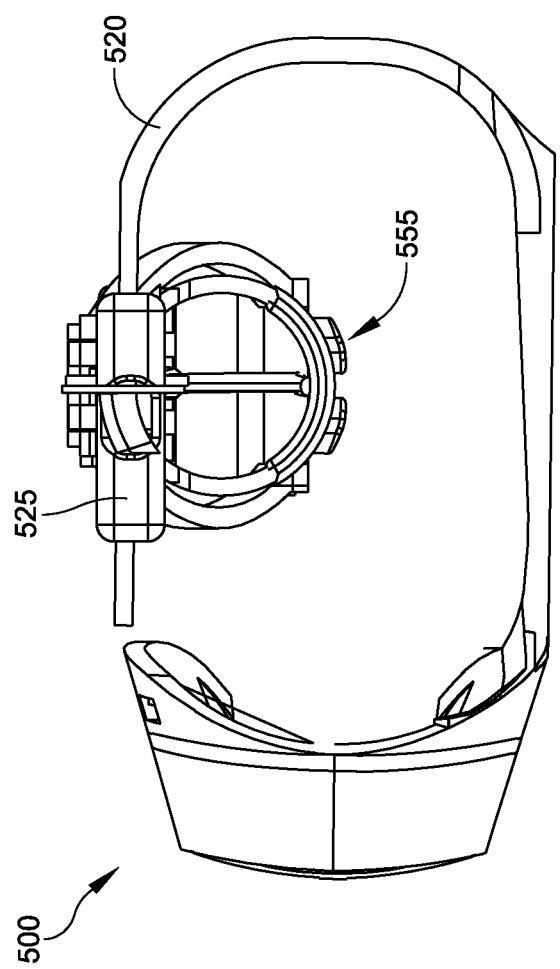
FIG. 6 is a front view of the prosthetic full finger assembly of FIG. 5.
Figure 7:
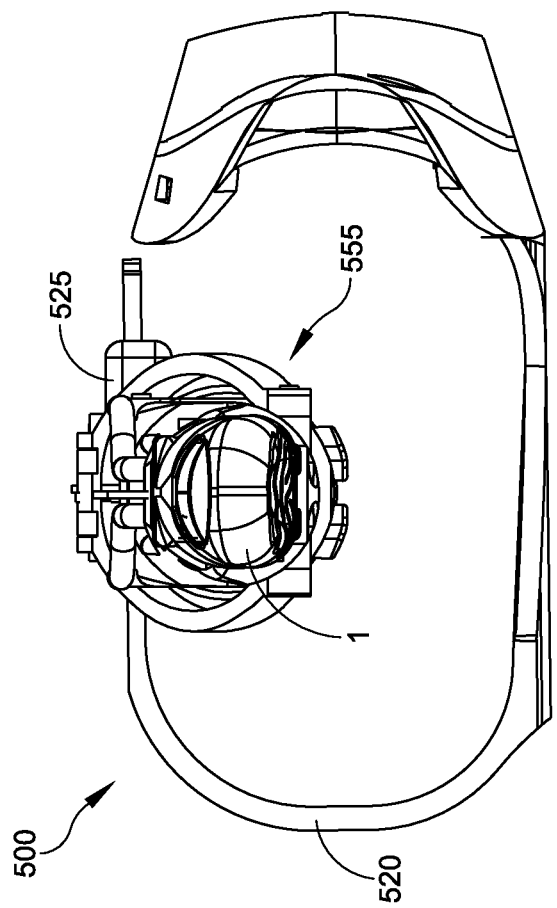
FIG. 7 is a rear view of the prosthetic full finger assembly of FIG. 5.

In reference to FIG. 4, the articulation cable 9 is connected to the proximal phalanges frame 32 and the lower distal surface. The articulation cable 9 is traversed through the middle phalanges 2 and contributes to the life-like natural movements of the prosthetic finger. The touch screen mechanism 10 comprises a conductive thread 101, and a conductive loop 103. The conductive thread 101 consists of a conductive material such as metal. The conductive loop 103 is the portion of the touch screen mechanism 10 that is used by the user to interact with the touch screen. The conductive loop 103 is made from a conductive material similar to the conductive thread 101. The conductive loop 103 is connected directly to the conductive thread 101. The conductive loop 103 is able to provide the user with the ability to interact with a touch screen at different angles. The distal phalanges 1 includes two holes and two channels able to allow the conductive loop to wrap around the tip of the distal phalanges 1. The two holes are positioned on a first distal corner and a second distal corner. Each of the holes are connected to a respective channel. The conductive loop 103 is traversed through the two channels and connects to the second thread. The conductive loop 103 is left with an exposed segment on the tip of the distal phalanges 1 for interaction with a touch screen. To ensure that the touch screen mechanism 10 fully draws the user's natural body current, the conductive thread 101 can be connected to the finger base brace 313 to ensure contact with the user's flesh. In other embodiments of the present invention, the conductive thread 101 can be connected anywhere on the prosthetic finger as long as it makes contact with a user's flesh.

The present invention provides a comfortable and natural movement for a user with an amputated finger. The design can be individually customized for users with varying amounts of loss on their finger. To further provide better aesthetics, the present invention can be coated with colorings to match the user's skin. The ease of use is another advantage of the present invention. To use the present invention, the user can simply slide the prosthetic finger onto the appropriate finger like a ring. To curl and bend the prosthetic finger the user can utilize the natural movements of the residual finger that the device is being worn on. The finger segments will articulate using the same cognitive process that was previously utilized for their original finger. Each of the prosthetic fingers can be independently operated. This means the user will be able to perform the activities including full typing, playing a musical instrument, or anything that requires the full dexterity of a hand. The present invention is fully powered by the user's own body. Each component of the prosthetic finger is able to move simply based on the actions of the user's residual finger. The present invention is designed to offer strength in the lowest profile design. As a result, the present invention naturally conforms with the looks of the user's hand.

Medical benefits of the present invention include uses of the device that reduce swelling and increases circulation, supporting the adjacent finger joints. The present device can be made out of Titanium, Stainless Steel, Aluminum, Silicone, Carbon Fiber, Nylon, Plastic, Wood, Rubber, Gold, Silver, Tungsten, Flex Cable, neoprene or any suitable structural material that is non-irritating to human skin. However, in the preferred embodiment of the present invention, the device is made from the material Duraform EX polymer material.

In another embodiment of the present invention, portions of the prosthetic finger can be used for differing conditions of the user. The present invention can be accommodated for fingertips or full fingers. The extended wishbone hinge 321 can be removed so that the prosthetic finger can be used as joint brace. Additionally, using biocompatible materials, the present invention can be applied as an orthopedic implant. Depending on the condition of the user, the present invention can be surgically implanted into the user's fingers. The use of the surgical implantation of the present invention can be applied for users having injuries that have crushed their bones without the ability to heal and be repaired. As a result, the present invention is able to take the place of the user's original bones without the need for amputation.

In one embodiment, the biomechanical prosthetic full finger 500 (BPFF 500) is a specifically designed, self-contained, prosthetic device for partial full finger or full fingertip amputees. It is an active-function artificial full fingertip. The natural action of the full finger assembly device allows users to regain maximum control of the flexion and extension movements of a full fingertip. It is designed to bend the prosthetic full fingertip in a realistic, natural manner.

The BPFF is a realistic tip, attached to a cap, which fits over the user's remaining full finger. The cap is attached to a ring providing stability during application and use. The five pieces have jointed or flexible connections supporting the smooth, natural turning or pivoting of the device.

Each BPFF device may be a custom designed and individually fitted prosthetic. The BPFF is made of any suitable structural material that is non-irritating to human skin, allowing the user to operate the prosthetic with comfort and confidence Features and User benefits of the present invention include but are not limited to the following:

Comfortable and natural movement and use. The design is based on an amount of finger loss, a number of joints to be replaced and other personal characteristics, including skin tone/color.

The user slides the BPFF device onto the appropriate finger like a ring, and bends the device using the natural movement of the remaining thumb. The thumb segments articulate using the same cognitive process previously used to articulate their thumb.

Everyone's individual uniqueness dictates the function and performance expected from their hands. Whether you are at work or play, independent control of each unit is individually designed and fitted. The BPFF is a custom fit device to fit the user allowing thumb is a necessity with today's lifestyles. We offer an active-function artificial finger assembly in a self-contained device. The BPFF will allow the user to regain control of the articulation of the device simply by moving their thumb. Benefits will include typing; playing a musical instrument or anything that requires the full dexterity of a hand Because the device is body powered, there is no need for external power supplies. The components articulate simply by moving the residual thumb when available or an opposing thumb when needed.

The components of the BPFF have been designed to not only look realistic during articulation, but to also bend a metal or silicone thumb tip in a realistic manner as well. The cable of the device when articulated, gently forces your new thumb tip to also bend in a natural manner.

The device has been designed to offer strength in the lowest profile design possible.

Medical benefits of the present invention include uses of the device that reduce swelling and increases circulation, supporting the adjacent finger joints. The present device can be made out of Titanium, Stainless Steel, Aluminum, Silicone, Carbon Fiber, Nylon, Plastic, Wood, Rubber, Gold, Silver, Tungsten, Flex Cable, neoprene or any suitable structural material that is non-irritating to human skin.

In various embodiments, the full finger 500 (BPFF) has approximately 3-4 parts added to a partial finger design. The ring part sits on the proximal phalanges, like the partial design. The ring part is attached to a metacarpal plate that sits on the back of the hand. Where the two pieces attach, there is a hinge. Above the hinge, there is another hinge with a part called the yoke. The other end of the yoke is attached to the bottom of the cap or cage (middle phalanges). So the full finger starts off in an extended position, just like the partial finger design. When the patient bends the metacarpal joint in their hand, the yoke pulls on the bottom of the cap or cage (middle phalanges) and then forcing the original mechanics of the partial to work. The metacarpal plate is held in place using the same thumb strap that the thumb is using. With the thumb strap, it will allow the patient to even wear the partial thumb design.

Figure 8:
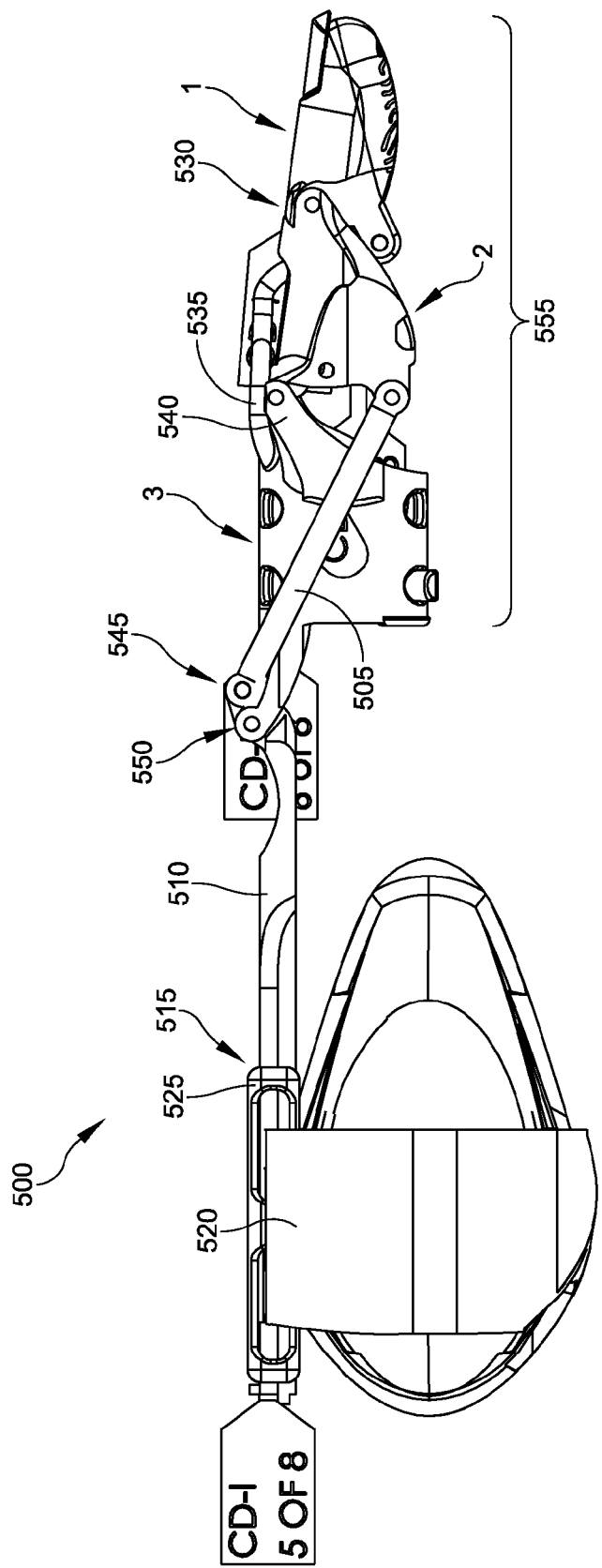
FIG. 8 is a right side view of the prosthetic full finger assembly of FIG. 5.
Figure 9:
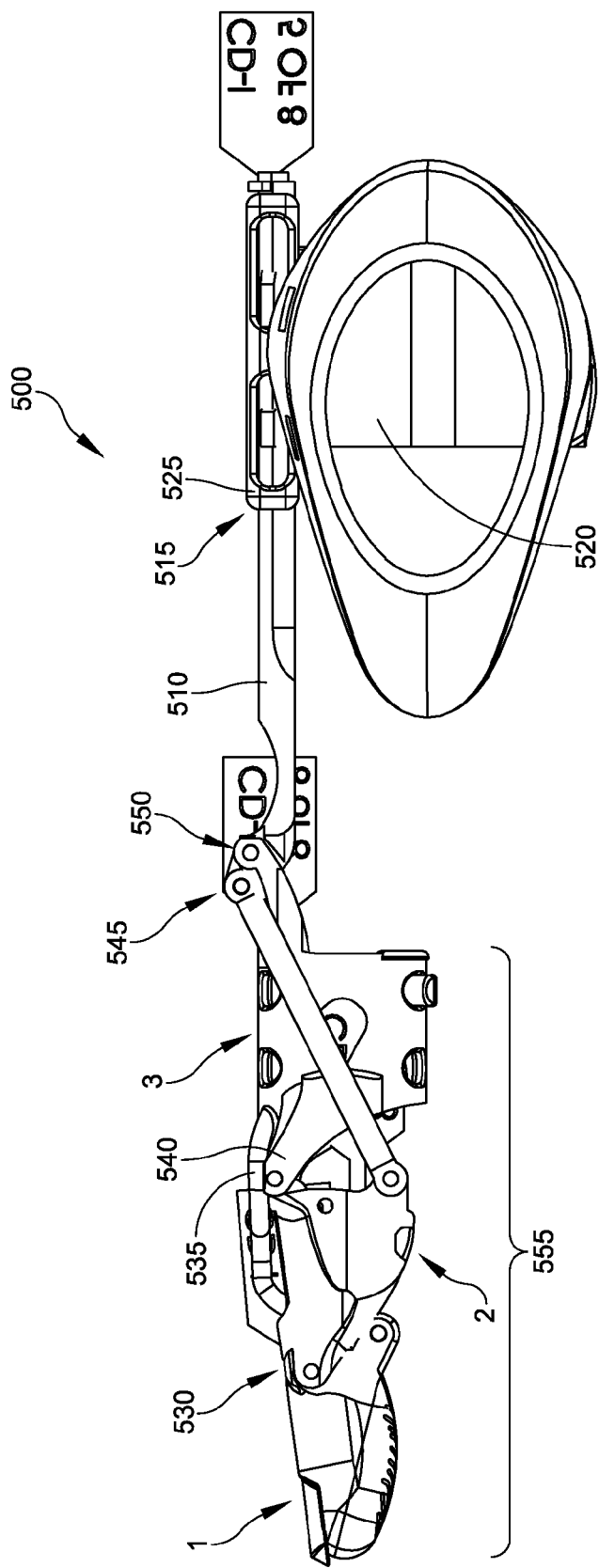
FIG. 9 is a left side view of the prosthetic full finger assembly of FIG. 5.
Figure 10:
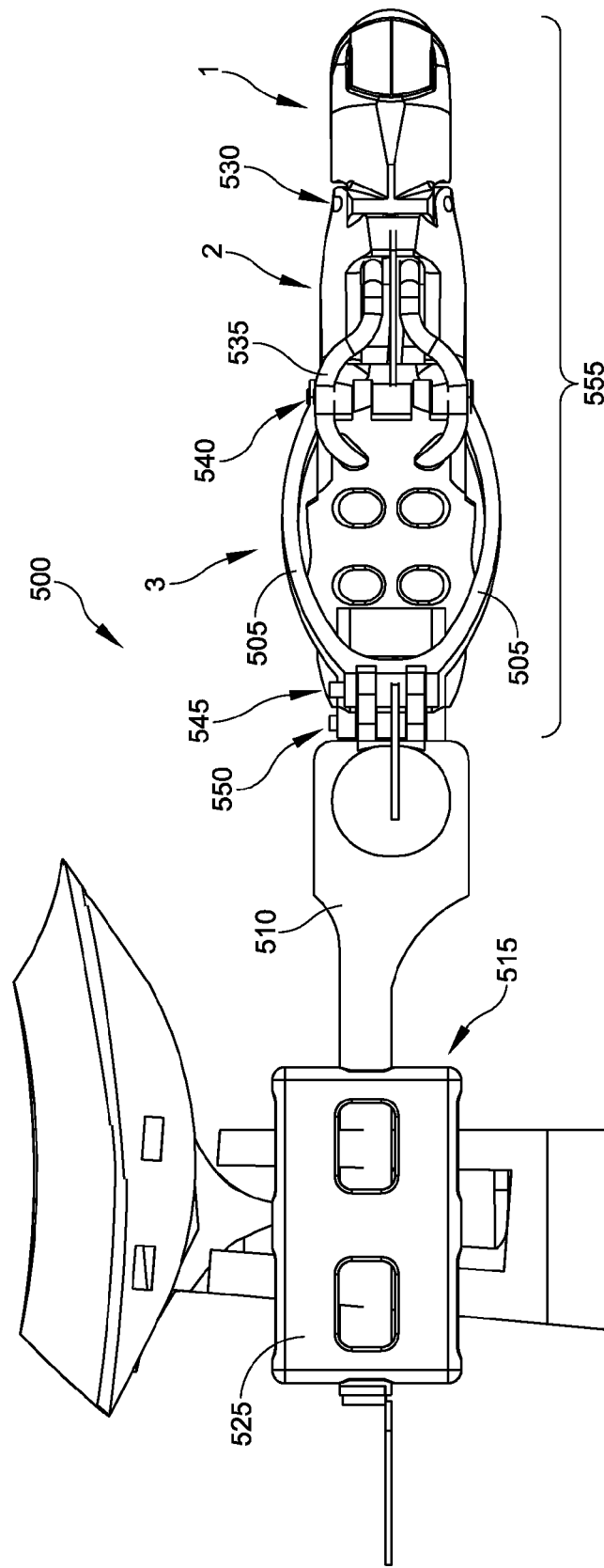
FIG. 10 is a top view of the prosthetic full finger assembly of FIG. 5.
Figure 11:
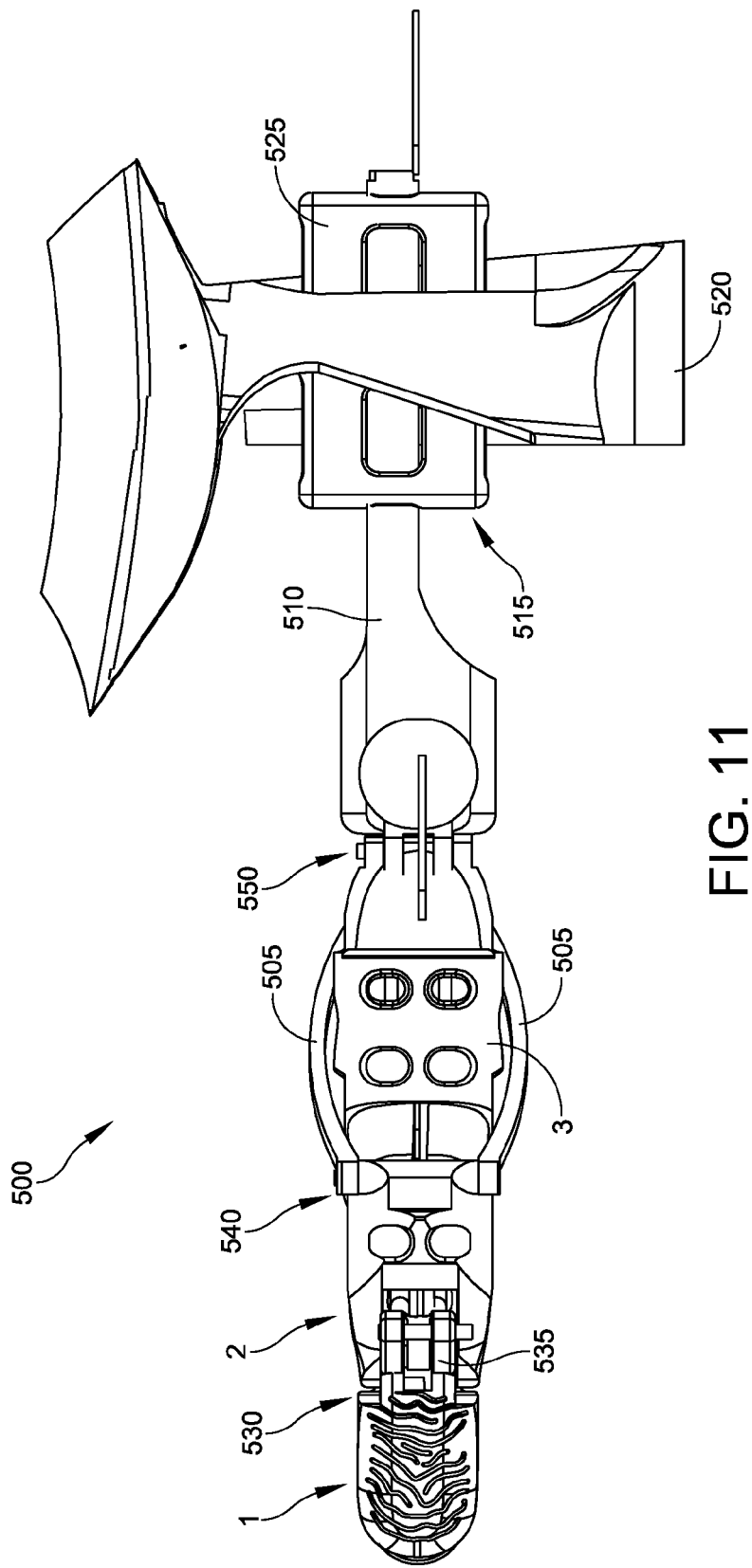
FIG. 11 is a bottom view of the prosthetic full finger assembly of FIG. 5.

Referring now to FIGS. 5-11, and in various embodiments, there is shown a prosthetic full finger assembly 500. In an embodiment, the full finger assembly 500 may include a distal phalanges 1. A middle phalanges 2, (which may be referred to as a cage) may be in operable connection with distal phalanges 1. This operable connection may include, but is not limited to, a hinge component. A proximal phalanges 3 (which may also be referred to as a ring or an index ring) may be in operable connection with the middle phalanges 2. A proximal phalanges yoke 505 may be in operable connection with the proximal phalanges 3, via a metacarpal back plate 510, as shown in FIGS. 8-9. The metacarpal back plate 510 may be in direct operable connection with each of the proximal phalanges ring 3 and the proximal phalanges yoke 505, thereby indirectly coupling the proximal phalanges 3 and the proximal phalanges yoke 505. An anchoring portion 515 may be in operable connection with the metacarpal back plate 510 at a location proximal of the operable connection of the proximal phalanges 3.

In one embodiment, the ring or proximal phalanges 3 may be placed on a proximal phalanges of the user. With the full finger assembly 500 in an extended position, similar to the partial finger design, the proximal phalanges yoke 505 is configured to pull on the middle phalanges cage 2 and force the original mechanics of the partial finger device portion to actuate when the user bends the metacarpal joint in his or her hand. In various embodiments, the metacarpal back plate 510 may be held in place using a thumb strap 520. This thumb strap 520 may be used with a thumb prosthetic device as well as the full finger assembly 500.

In one embodiment, the anchoring portion 515 may include a thumb strap 520. The thumb strap may include a grommet anchor 525.

The operable connection of the middle phalanges 2 with the distal phalanges 1 may include a pair of distal hinges 530 and a proximal pulling hinge 535. The operable connection of the proximal phalanges ring 3 with the middle phalanges 2 may include a pair of proximal hinges 540.

The operable connection of the metacarpal back plate 510 with the proximal phalanges yoke 505 is a hinge 545 adjacent a distal end of the metacarpal back plate 510 and adjacent a proximal end of the proximal phalanges yoke 505.

The operable connection of the metacarpal back plate 510 with the proximal phalanges ring 3 is a hinge 550 adjacent the distal end of the metacarpal back plate 510 and adjacent a proximal end of the proximal phalanges ring 3.

In another embodiment, there is disclosed a prosthetic full finger assembly 500 with a distal phalanges 1 having an operable connection 530 at its proximal end. A metacarpal back plate 510 may have an operable connection adjacent a distal end thereof and an anchor adjacent a proximal end thereof. Articulation components 555 may be configured between the metacarpal back plate 510 and the distal phalanges 1. In various embodiments, the metacarpal back plate 510 may be configurable for placement on a back portion of a hand, and when a metacarpal joint in the hand is bent the articulation components are articulated to articulate the distal phalanges 1.

Although the above embodiments have been described in language that is specific to certain structures, elements, compositions, and methodological steps, it is to be understood that the technology defined in the appended claims is not necessarily limited to the specific structures, elements, compositions and/or steps described. Rather, the specific aspects and steps are described as forms of implementing the claimed technology. Since many embodiments of the technology can be practiced without departing from the spirit and scope of the invention, the invention resides in the claims hereinafter appended.

What is claimed is:

1. A prosthetic full finger assembly, comprising:
   a distal phalanges;
   a middle phalanges having a direct pivoting connection with the distal phalanges;
   a proximal phalanges ring having a direct pivoting connection with the middle phalanges;
   a proximal phalanges yoke having a proximal end and a distal end, the distal end of the proximal phalanges yoke having a direct pivoting connection with the middle phalanges;
   a metacarpal back plate having a proximal end and a distal end, the distal end of the metacarpal back plate having a first direct pivoting connection with the proximal end of the proximal phalanges yoke and a second direct pivoting connection with the proximal phalanges ring, thereby forming an indirect pivoting connection between the proximal phalanges ring and the proximal phalanges yoke; and
   an anchoring portion having an operable connection with the proximal end of the metacarpal back plate.

2. The assembly of claim 1, wherein the anchoring portion includes a thumb strap.

3. The assembly of claim 2, wherein the thumb strap includes a grommet anchor.

4. The assembly of claim 1, wherein the direct pivoting connection of the middle phalanges with the distal phalanges includes a pair of distal hinges and a proximal pulling hinge.

5. The assembly of claim 1, wherein the direct pivoting connection of the proximal phalanges ring with the middle phalanges includes a pair of proximal hinges.

6. The assembly of claim 1, wherein the first direct pivoting connection of the distal end of the metacarpal back plate with the proximal end of the proximal phalanges yoke is a hinge adjacent the distal end of the metacarpal back plate and adjacent the proximal end of the proximal phalanges yoke.

7. The assembly of claim 1, wherein the second direct pivoting connection of the distal end of the metacarpal back plate with the proximal phalanges ring is a hinge adjacent the distal end of the metacarpal back plate and adjacent a proximal end of the proximal phalanges ring.

8. The assembly of claim 1, wherein when the prosthetic full finger assembly is in use, the distal phalanges, the middle phalanges, the proximal phalanges ring, and the proximal phalanges yoke fit concentrically about a user's residual proximal phalanges.

9. A prosthetic full finger assembly for a user's residual finger, comprising:
   a distal phalanges having a pivoting connection at a proximal end thereof;
   a metacarpal back plate having a pivoting connection adjacent a distal end thereof and an anchor adjacent a proximal end thereof; and
   articulation components configured between the distal end of the metacarpal back plate and the distal phalanges, the articulation components configured to articulate the distal phalanges in response to articulation of a metacarpal joint of the user's residual finger, wherein:
   the pivoting connection adjacent the distal end of the metacarpal back plate comprises first and second pivoting connections between the articulation components and the distal end of the metacarpal back plate; and
   the metacarpal back plate is configurable for placement on a back portion of a hand, and when the metacarpal joint of the user's residual finger is bent, the articulation components are articulated to articulate the distal phalanges.

10. The assembly of claim 9, wherein the anchor includes a thumb strap.

11. The assembly of claim 10, wherein the thumb strap includes a grommet anchor.

12. The assembly of claim 9, wherein the articulation components comprise:
   a middle phalanges having a direct pivoting connection with the distal phalanges;
   a proximal phalanges ring having a direct pivoting connection with the middle phalanges; and
   a proximal phalanges yoke having a proximal end and a distal end, wherein:
   the first pivoting connection between the articulation components and the distal end of the metacarpal back plate comprises a direct pivoting connection between the distal end of the metacarpal back plate and the proximal end of the proximal phalanges yoke; and
   the second pivoting connection between the articulation components and the distal end of the metacarpal back plate comprises a direct pivoting connection between the distal end of the metacarpal back plate and the proximal phalanges ring.

13. The assembly of claim 12, wherein the direct pivoting connection between the middle phalanges and the distal phalanges includes a pair of distal hinges and a proximal pulling hinge.

14. The assembly of claim 12, wherein the direct pivoting connection between the proximal phalanges ring and the middle phalanges includes a pair of proximal hinges.

15. The assembly of claim 12, wherein the direct pivoting connection between the distal end of the metacarpal back plate and the proximal end of the proximal phalanges yoke includes a hinge.

16. The assembly of claim 12, wherein the direct pivoting connection between the distal end of the metacarpal back plate and the proximal phalanges ring comprises a hinge.

\* \* \* \* \*